United States Patent [19] [11] 4,270,923
Kondo et al. [45] Jun. 2, 1981

[54] PRETREATMENT AGENT FOR SUBJECT FLUID IN PREGNANCY TEST

[75] Inventors: Koichi Kondo, Osaka; Isamu Yoshida, Takatsuki; Takashi Kobayashi, Hikari, all of Japan

[73] Assignee: Takeda Chemical Industries, Ltd., Osaka, Japan

[21] Appl. No.: 107,179

[22] Filed: Dec. 26, 1979

[30] Foreign Application Priority Data

Dec. 25, 1978 [JP] Japan ................................. 53-160762

[51] Int. Cl.³ ............................................. G01N 33/76
[52] U.S. Cl. .................... 23/230 B; 23/914; 23/915; 23/917; 210/927; 210/500.1; 422/101; 424/3; 424/12
[58] Field of Search ...................... 23/230 B, 914, 915, 23/917; 210/DIG. 23, 502, 500 R; 55/522, 524, 528; 424/12, 3; 422/101, 69; 252/408

[56] References Cited

U.S. PATENT DOCUMENTS

| 3,171,783 | 3/1965 | Fisk | 23/230 B X |
| 3,215,500 | 11/1965 | Bittner | 422/101 |
| 3,594,993 | 7/1971 | Heyse | 55/524 |
| 3,873,682 | 3/1975 | Ogawa | 424/12 |
| 3,901,657 | 8/1975 | Lightfoot | 252/408 X |
| 4,138,214 | 2/1979 | Givner | 23/230 B |
| 4,160,644 | 7/1979 | Ryan | 424/3 X |

Primary Examiner—Arnold Turk
Attorney, Agent, or Firm—Wenderoth, Lind & Ponack

[57] ABSTRACT

By using a new pretreatment agent consisting essentially of a carboxylic acid-type cation exchange resin fiber or a siliconized glass fiber, the interfering components and the elements of turbidity present in a subject fluid for immunologic pregnancy test can be specifically removed without entailing a substantial loss of human chorionic gonadotropin contained in the subject fluid.

6 Claims, No Drawings

PRETREATMENT AGENT FOR SUBJECT FLUID IN PREGNANCY TEST

The present invention relates to an improvement in the pretreatment of subject fluids for immunologic pregnancy tests.

Immunologic tests have been used for the diagnosis of pregnancy, which estimate the human chorionic gonadotropin (hereinafter briefly, HCG) in the urine or body fluid (serum, plasma, etc.) of a pregnant woman.

The principle of the anti-HCG antibody-sensitized latex agglutination test (latex direct agglutination reaction; hereinafter briefly, LDAR) is that as a latex particles carrying anti-HCG antibodies as adsorbed thereon are admixed with a subject urine, serum or plasma sample, the latex particles are agglutinated if HCG is present in the sample, the detection of such agglutination establishing a diagnosis of pregnancy. On the other hand, the principle of the HCG-sensitized latex agglutination inhibition test (latex agglutination inhibition reaction; hereinafter briefly, LAIR), is that as a latex carrying HCG as adsorbed thereon is admixed with a given amount of an anti-HCG antiserum, the latex particles are agglutinated, but if the latex is added after admixture of an HCG-containing subject fluid with a given amount of anti-HCG antiserum, the latex will not be agglutinated because the anti-HCG antibody has already been coupled to the HCG in the subject fluid. This, in LAIR the absence of latex agglutination establishes a diagnosis of pregnancy. Another method is the hemagglutination inhibition test (hereinafter briefly, HAIR) in which a diagnosis of pregnancy is performed using HCG-sensitized human or animal red blood cells in place of latex particles.

These immunologic pregnancy tests tend to give false results in early stages of pregnancy because the secretion of HCG in this period is so small that only a weak agglutination (or inhibition) reaction takes place. Moreover, sensitized latex and sensitized red blood cells may undergo non-specific reactions independently of the immunologic reaction of HCG with the anti-HCG antibody. Therefore, when the urine or serum containing a variety of components is assayed by the above methods, the agglutination (or inhibition) reaction is interfered with by components other than HCG in the sample to lead to a false diagnosis.

Subject fluids could also be turbid and if such fluids are directly assayed, false results may ensue. To prevent such false results, the fluids are usually filtered prior to the agglutination (inhibition) reaction.

The filter materials conventionally employed are cellulosic filter paper, absorbent cotton, cellulose acetate, polyacrylonitrile, carboxylmethylcellulose and other fiber but none of them is fully satisfactory. For instance, cellulosic filter paper and absorbent cotton are capable of removing the turbidity but have the disadvantage that HCG is also adsorbed. Cellulose acetate and polyacrylonitrile fiber are not efficient enough to thoroughly remove interferring components. While fibrous carboxylmethylcellulose is highly capable of removing the turbidity and interfering components, it entails adsorption of HCG.

With the above technical difficulties by way of background, the present inventors have unexpectedly found that the interfering components and the elements of turbidity present in the subject fluids can be specifically removed without entailing a substantial loss of HCG by contacting the subject fluids with a carboxylic acid-type cation exchange resin fiber or a siliconized glass fiber.

Thus, the principal object of the present invention is to provide an excellent agent for pretreating a subject fluid for pregnancy tests by means of an immunologic assay of HCG, which consists essentially of a carboxylic acid-type cation exchange resin fiber or a siliconized glass fiber. Another object is to provide an improved method for pretreating the subject fluids with use of said agent. Other objects will be made clear from the description and claims hereinafter.

The carboxylic acid-type cation exchange resin fiber used in this invention preferably has a cation exchange capacity of at least about 1.5 meq/g and, especially, about 5 to 8 meq/g. For example, a preferable fiber may be prepared by reacting a polymer molding containing at least 40 weight percent of acrylonitrile with hydrazine or a homolog of hydrazine to provide said polymer molding with an anion exchange capacity of 0.01 to 3.0 meq/g and, then, hydrolyzing the residual nitrile groups with alkali or mineral acid to introduce cation-exchanging groups into the molding (cf. Japanese Patent Application Laid-Open No. 14389/1974 (Tokukai Sho 49-14389)).

The siliconized glass fiber may be prepared by treating an ordinary glass fiber with a compound of silicon or a silicon-containing composition such as silane coupling agents (organofunctional silanes), silicone oil, silicone oil emulsion, silicone varnish, silicone varnish emulsion, etc. This siliconization treatment is generally carried out by impregnating a glass fiber with an aqueous or organic solvent solution of said compound of silicon or silicon-containing composition and heating the fiber (usually at about 100° to 300° C.).

The carboxylic acid-type cation exchange resin fiber and siliconized glass fiber may be used alone or in combination. The carboxylic acid-type cation exchange resin fiber is advantageously used in the form of filament or staple fiber (preferably 0.1 to 2 mm in length) with a denier number of about 2 to 15. The siliconized glass fiber is preferably used in the form of filament with a diameter of about 5 to 15 $\mu$m.

In contacting the subject fluid, such as the urine, serum or plasma of a woman, with the above-mentioned fiber, the fluid may be filtered through a layer of the fiber or, alternatively, the fluid may be admixed with the fiber and then separated (by filtration, centrifugal separation, etc.), although it is generally preferable to filter the subject fluid through the fibrous layer. A typical filtration procedure is as follows. A tube (preferably made from polyethylene) is packed with about 20 to 100 mg, most preferably about 50 mg, of said fiber and connected to the lower end of a pipe (preferably made from polyethylene) fitted with a rubber suction cap. Then, the tube is dipped into the subject fluid and the rubber cap is squeezed to fill the suction pipe with a suitable quantity (about 0.3 ml) of the test fluid to obtain a filtrate. The tube is disconnected and the filtrate is directly used for the pregnancy diagnostic test. For instance, two drops of the above filtrate are dripped on a clean glass plate for LDAR or LAIR, or a HAIR test is carried out with 0.1 ml in a test tube.

The present invention further provides a kit for the pretreatment of the subject fluids, which comprises a tube packed with about 20 to 100 mg of the carboxylic acid-type cation exchange resin fiber or a siliconized glass fiber, and a pipe fitted with a rubber suction cap, to which said tube is to be connected at its lower end.

The pretreatment according to this invention removes the interfering components and turbidity elements without causing any substantial loss of HCG in the subject fluid, thus leading to remarkable improvements in sensitivity and reliability of the pregnancy test, especially LDAR.

The beneficial results of this invention will be further explained by the following tests and working examples.

The carboxylic acid-type cation exchange resin fiber and siliconized glass fiber used in these tests and examples are as follows:

The carboxylic acid-type cation exchange resin fiber was prepared by the procedure described in Example 1 of Japanese Patent Application Laid-Open No. 14389/1974. It has a triazine-or tetrazine-cross linked structure and a cation exchange capacity of 6.4 meq/g, and is a pale-pinkish in appearance. In the infrared region of the spectrum this fiber showed a strong carbonyl band at 1600–1700 cm$^{-1}$ but showed no nitrile absorption (2250 cm$^{-1}$). This resin fiber was used in the form of filament with 6 denier except Example 4 wherein it was used in the form of staple fiber of 1 mm inn length with 3 denier.

The siliconized glass fiber was prepared as follows. A glass fiber with a diameter of about 10 μm was dewaxed with acetone and diethyl ether, immersed in a 1% solution of dimethylpolysiloxane in trichloroethylene for one minute, heat-treated at 200° C. for one hour and finally washed with 20% ethanol.

In the following tests and examples, LDAR and HAIR tests were respectively performed in conformity with the procedures described in the following literature:

LDAR test: J. Pharm. Soc. Japan, 98, 376(1978)
HAIR test: Acta Endocr. (Kbh), Suppl. 70(1962)

TEST EXAMPLE 1

Lower portions of polyethylene tubes with an inside diameter of 5 mm and a height of 45 mm were respectively packed with 50 mg of the above fibers according to this invention and the filtration procedure described hereinbefore was followed to obtain 0.3 ml of filtered urine or serum. As the cellulosic filter paper, Toyo Filter No. 50 (dia. 5.5 cm, wt. 237 mg) was used. The paper was pursed and placed over a funnel and 1.5 ml of urine or serum was passed.

As regards subject fluids, 10 urine specimens, with especially high degrees of interference, from those of nonpregnant women were selected. The five serum specimens from nonpregnant women were also employed. Each specimen was filtered as described hereinbefore and submitted to LDAR and HAIR tests. As controls, unfiltered samples were also tested. The results are presented in Table 1 and 2 appearing later.

The unfiltered urine specimens of nonpregnant women used in these tests showed overtly positive results in 5 out of 10 cases in LDAR, with the remaining 5 cases giving doubtful-positive results, i.e. intermediate between negative and positive reactions. In HAIR, one case was positive and 3 cases were doubtful positive. The influence of components leading to false results is particularly evident in LDAR but their incidence is reduced by filtration. The incidences of false results with various filter materials, when doubtful-positive results were added to positive results, were as follows. Cellulosic filter paper 5/10; absorbent cotton 5/10; wool 3/10; untreated glass fiber 3/10; viscose rayon 5/10; nylon 5/10; polyester 5/10; polypropylene 5/10; polyvinyl chloride 5/10; polyacrylonitrile 3/10; polyurethane 4/10; cellulose acetate 2/10; carboxymethylcellulose 1/10.

When the carboxylic acid-type cation exchange resin fiber or siliconized glass fiber was employed, all cases were found to be negative. In HAIR runs using filtered urine, all cases were found to be negative. The results of LDAR runs on nonpregnant sera, filtered through different filters, are shown in Table 3. Without filtration, the incidence of false results was 2/5 but with filtered sera all specimens were found to be negative, irrespective of the filter materials employed.

As mentioned above, when tests are carried out on unfiltered urine or serum, specimens which ought to be negative tend to give positive reactions, thus leading to misdiagnoses. Moreover, even with cellulosic filter paper, absorbent cotton, untreated glass, viscose rayon, nylon, polyester, polypropylene, polyvinyl chloride, polyacrylonitrile, polyurethane, cellulose acetate or carboxymethylcellulose fibers etc., specimens which ought to be negative sometimes produce positive results, thus leading again to misdiagnoses.

LDAR tests were performed on 10 urine samples from women in early stages of pregnancy which were lean in HCG. The results are shown in Table 4. When the urine samples were not filtered, all cases were found to be positive. However, when specimens were filtered through cellulosic filter paper or absorbent cotton, the reaction was considerably weakened so that pregnant women who ought to be positive were falsely found to be nonpregnant. With viscose rayon and carboxymethylcellulose, the incidence of false results was 2/10. The reaction was invariably weak when wool, untreated glass fiber, nylon, polyester, polypropylene, polyvinyl chloride and polyurethane were employed, the incidence of false results being 1/10 for each. In contrast, all cases were found to be positive with the carboxylic acid-type cation exchange resin and siliconized glass fibers according to this invention as well as with polyacrylonitrile and cellulose acetate.

It is necessary to filter subject fluids in order to remove turbidity and interfering components. However, depending on the kind of filter material, the HCG in the test fluid is adsorbed on the filter to cause a misdiagnosis.

When the carboxylic acid-type cation exchange resin or siliconized glass fiber is employed, substantially no HCG adsorption takes place. Moreover, the filters of this invention effectively remove the components which would interfere with the reactions. Thus, they reduce considerably the incidence of misdiagnosing nonpregnancy as pregnancy.

TEST EXAMPLE 2

HCG was added to 3 urine samples from healthy nonpregnant women to give an HCG concentration of one I.U./ml, and each sample was filtered as described hereinbefore. The residual HCG (%) in each filtered urine sample was measured by radioimmunoassay.

As shown in Table 5, cellulosic filter paper, absorbent cotton, wool, untreated glass fiber, viscose rayon, nylon, polyester, polypropylene, polyvinyl chloride, polyurethane and carboxymethylcellulose showed up to 65% adsorption of HCG. Substantially no adsorption of HCG occurred with carboxylic acid-type cation exchange resin fiber, siliconized glass fiber, cellulose acetate or polyacrylonitrile fiber.

EXAMPLE 1

Polyethylene tubes, 5.0 mm in inside diameter, were respectively packed with 50 mg of carboxylic acid-type cation exchange resin fiber or siliconized glass fiber of the present invention, absorbent cotton, cellulose acetate fiber, polyacrylonitrile fiber and carboxymethylcellulose fiber and 400 urine samples from nonpregnant women were filtered with the above tubes by the procedure described hereinbefore, to obtain 0.3 ml of filtered urine from each urine sample. Two drops of each filtered urine sample were subjected to the LDAR tests.

As shown in Table 6 appearing later, for the urine samples filtered through absorbent cotton, 10 out of 400 samples showed positive reactions and 35 doubtful-positive reactions; with cellulose acetate, 7 positive and 8 doubtful-positive; with polyacrylonitrile, 7 positive and 13 doubtful-positive. With carboxymethylcellulose, too, 1 showed positive reaction and 2 doubtful-positive reactions. On the contrary, with the carboxylic acid-type cation exchange resin fiber or siliconized glass fiber, all the samples (400 samples) gave negative results. In this manner those components which possibly interfere with the diagnostic reaction can be removed to a very great extent by the method of the present invention.

EXAMPLE 2

Urine samples from 200 women definitely diagnosed as pregnant by clinical diagnoses were subjected to the LDAR test after filtration under the same conditions as in Example 1 using the carboxylic acid-type cation exchange resin fiber or siliconized glass fiber of the present invention or absorbent cotton, cellulose acetate fiber, polyacrylonitrile fiber or carboxymethylcellulose fiber.

As shown in Table 7 appearing later, in the case of absorbent cotton, polyacrylonitrile and carboxymethylcellulose, 10, 3 and 3 cases, respectively, were erroneously diagnosed as nonpregnant. When the carboxylic acid-type cation exchange resin fiber was used as the filter material according to the invention, all the samples reacted positively in accord with the results of the definite clinical diagnosis. Also in the case where the siliconized glass fiber was used, all the cases showed positive results except for one case in which the reaction was doubtful-positive.

EXAMPLE 3

Serum samples from 50 nonpregnant women and 50 pregnant women were filtered through the carboxylic acid-type cation exchange resin fiber or siliconized glass fiber used as a filter material under the same conditions as in Example 1 and two drops of each filtered serum sample were subjected to the LDAR test. All the serum samples from nonpregnant women reacted negatively, while all the serum samples from pregnant women showed positive reactions.

EXAMPLE 4

Urine samples from 50 nonpregnant women and 50 pregnant women were filtered through the carboxylic acid-type cation exchange resin staple fiber of 1 mm in length with 3 denier used as a filter material under the same conditions as in Example 1 and two drops of each filtered urine samples were subjected to the LDAR test. All the urine samples from nonpregnant women reacted negatively, while all the urine sample from pregnant women showed positive reactions.

TABLE 1

Comparison of different pretreatments of urine samples from nonpregnant women (LDAR)

| Pretreatment | 1 | 2 | 3 | 4 | 5 | 6 | 7 | 8 | 9 | 10 |
|---|---|---|---|---|---|---|---|---|---|---|
| Without filtration | + | + | ± | ± | + | ± | ± | ± | + | + |
| Filtration through | | | | | | | | | | |
| Cellulosic filter paper | − | + | − | ± | − | − | ± | − | ± | + |
| Absorbent cotton | − | + | − | ± | − | − | ± | − | ± | + |
| Wool | − | + | − | − | − | − | − | − | ± | + |
| Untreated glass fiber | − | + | − | − | − | − | − | − | ± | + |
| Viscose rayon | − | + | − | ± | − | − | ± | − | ± | + |
| Nylon | − | + | − | ± | − | − | ± | − | ± | + |
| Polyester | − | + | − | ± | − | − | ± | − | + | + |
| Polypropylene | − | + | − | ± | − | − | ± | − | + | + |
| Polyvinyl chloride | − | ± | − | ± | − | − | ± | − | + | + |
| Polyacrylonitrile | − | ± | − | − | − | − | − | − | ± | + |
| Polyurethane | − | + | − | − | − | − | ± | − | ± | + |
| Cellulose acetate | − | − | − | − | − | − | − | − | ± | + |
| Carboxymethylcellulose | − | − | − | − | − | − | − | − | − | + |
| Carboxylic acid-type cation exchange resin fiber | − | − | − | − | − | − | − | − | − | − |
| Siliconized glass fiber | − | − | − | − | − | − | − | − | − | − |

Remarks:
+ Positive results
± Doubtful-position results
− Negative results
(The same shall apply hereinafter.)

TABLE 2

Comparison of different pretreatments of urine samples from nonpregnant women (HAIR)

| Pretreatment | 1 | 2 | 3 | 4 | 5 | 6 | 7 | 8 | 9 | 10 |
|---|---|---|---|---|---|---|---|---|---|---|
| Without filtration | − | ± | − | − | − | − | − | ± | ± | + |
| Filtration through | | | | | | | | | | |
| Cellulosic filter paper | − | − | − | − | − | − | − | − | − | − |
| Absorbent cotton | − | − | − | − | − | − | − | − | − | − |
| Wool | − | − | − | − | − | − | − | − | − | − |
| Untreated glass fiber | − | − | − | − | − | − | − | − | − | − |
| Viscose rayon | − | − | − | − | − | − | − | − | − | − |
| Nylon | − | − | − | − | − | − | − | − | − | − |
| Polyester | − | − | − | − | − | − | − | − | − | − |
| Polypropylene | − | − | − | − | − | − | − | − | − | − |
| Polyvinyl chloride | − | − | − | − | − | − | − | − | − | − |
| Polyacrylonitrile | − | − | − | − | − | − | − | − | − | − |
| Polyurethane | − | − | − | − | − | − | − | − | − | − |
| Cellulose acetate | − | − | − | − | − | − | − | − | − | − |
| Carboxymethylcellulose | − | − | − | − | − | − | − | − | − | − |
| Carboxylic acid-type cation exchange resin fiber | − | − | − | − | − | − | − | − | − | − |
| Siliconized glass fiber | − | − | − | − | − | − | − | − | − | − |

TABLE 3

Comparison of different pretreatments of serum samples from nonpregnant women (LDAR)

| Pretreatment | 1 | 2 | 3 | 4 | 5 |
|---|---|---|---|---|---|
| Without filtration | − | − | ± | − | + |
| Filtration through | | | | | |
| Cellulosic filter paper | − | − | − | − | − |
| Absorbent cotton | − | − | − | − | − |
| Wool | − | − | − | − | − |
| Untreated glass fiber | − | − | − | − | − |
| Viscose rayon | − | − | − | − | − |
| Nylon | − | − | − | − | − |
| Polyester | − | − | − | − | − |
| Polypropylene | − | − | − | − | − |
| Polyvinyl chloride | − | − | − | − | − |
| Polyacrylonitrile | − | − | − | − | − |
| Polyurethane | − | − | − | − | − |

TABLE 3-continued

Comparison of different pretreatments of serum samples from nonpregnant women (LDAR)

| Pretreatment | Serum No. 1 | 2 | 3 | 4 | 5 |
|---|---|---|---|---|---|
| Cellulose acetate | − | − | − | − | − |
| Carboxymethylcellulose | − | − | − | − | − |
| Carboxylic acid-type cation exchange resin fiber | − | − | − | − | − |
| Siliconized glass fiber | − | − | − | − | − |

TABLE 4

Comparison of different pretreatments of urine samples from women in early stages of pregnancy

| Pretreatment | 1 | 2 | 3 | 4 | 5 | 6 | 7 | 8 | 9 | 10 |
|---|---|---|---|---|---|---|---|---|---|---|
| Without filtration | + | + | + | + | + | + | + | + | + |  |
| Filtration through |  |  |  |  |  |  |  |  |  |  |
| Cellulosic filter paper | + | − | + | + | ± | − | − | + | ± | − |
| Absorbent cotton | + | − | + | + | ± | − | − | + | − | − |
| Wool | + | + | + | + | + | + | + | + | ± | − |
| Untreated glass fiber | + | + | + | + | + | + | + | + | ± | − |
| Viscose rayon | + | ± | + | + | ± | − | ± | + | ± | − |
| Nylon | + | + | + | + | + | + | + | + | ± | − |
| Polyester | + | + | + | + | + | + | + | + | ± | − |
| Polypropylene | + | + | + | + | + | + | + | + | ± | − |
| Polyvinyl chloride | + | + | + | + | + | + | + | + | ± | − |
| Polyacrylonitrile | + | + | + | + | + | + | + | + | + | ± |
| Polyurethane | + | + | + | + | + | + | + | + | ± | − |
| Cellulose acetate | + | + | + | + | + | + | + | + | + | + |
| Carboxymethylcellulose | + | + | + | + | + | − | + | + | ± | − |
| Carboxylic acid-type cation exchange resin fiber | + | + | + | + | + | + | + | + | + | + |
| Siliconized glass fiber | + | + | + | + | + | + | + | + | + | + |

TABLE 5

Residual HCG (%) in filtered urine samples

| Pretreatment | Urine No. 1 | 2 | 3 |
|---|---|---|---|
| Filtration through |  |  |  |
| Cellulosic filter paper | 47 | 45 | 50 |
| Absorbent cotton | 41 | 35 | 40 |
| Wool | 62 | 65 | 59 |
| Untreated glass fiber | 55 | 60 | 60 |
| Viscose rayon | 40 | 40 | 35 |
| Nylon | 92 | 85 | 88 |
| Polyester | 79 | 80 | 80 |
| Polypropylene | 85 | 80 | 75 |
| Polyvinyl chloride | 90 | 88 | 88 |
| Polyacrylonitrile | 100 | 95 | 97 |
| Polyurethane | 95 | 86 | 90 |
| Cellulose acetate | 100 | 99 | 98 |
| Carboxymethylcellulose | 56 | 60 | 65 |
| Carboxylic acid-type cation exchange resin fiber | 100 | 101 | 100 |
| Siliconized glass fiber | 100 | 96 | 99 |

TABLE 6

Comparison of different pretreatments of urine samples from 400 nonpregnant women

| Pretreatment | Positive | Doubtful-positive | Negative |
|---|---|---|---|
| Filtration through |  |  |  |
| Absorbent cotton | 10 | 35 | 355 |
| Cellulose acetate | 7 | 8 | 385 |
| Polyacrylonitrile | 7 | 13 | 380 |
| Carboxymethylcellulose | 1 | 2 | 397 |
| Carboxylic acid-type cation exchange resin fiber | 0 | 0 | 400 |
| Siliconized glass fiber | 0 | 0 | 400 |

TABLE 7

Comparison of different pretreatments of urine samples from 200 pregnant women

| Pretreatment | Positive | Doubtful-positive | Negative |
|---|---|---|---|
| Filtration through |  |  |  |
| Absorbent cotton | 181 | 9 | 10 |
| Cellulose acetate | 195 | 2 | 3 |
| Polyacrylonitrile | 193 | 4 | 3 |
| Carboxymethylcellulose | 189 | 6 | 5 |
| Carboxylic acid-type cation exchange resin fiber | 200 | 0 | 0 |
| Siliconized glass fiber | 199 | 1 | 0 |

What is claimed is:

1. A method for pretreating a subject fluid for a pregnancy test by means of an immunologic assay of human chorionic gonadotropin, which comprises removing the interfering components and turbidity from the subject fluid by contacting the subject fluid with a carboxylic acid-type cation exchange resin fiber having a cation exchange capacity of about 5 to 8 meq/g or a siliconized glass fiber prepared by impregnating a glass fiber with a solution of dimethylpolysiloxane and heating the fiber.

2. A method according to claim 1, wherein the subject fluid is woman's urine or serum.

3. A method according to claim 1, wherein the subject fluid is filtered through a layer of the carboxylic acid-type cation exchange resin fiber or the siliconized glass fiber.

4. A method according to claim 3, wherein the resin fiber is in the form of filament or staple fiber with a denier number of about 2 to 15.

5. A method according to claim 3, wherein the layer is of the siliconized glass fiber in the form of filament with a diameter of about 5 to 15 μm.

6. A method according to claim 3, wherein the amount of the fibrous layer is about 20 to 100 mg per 0.3 ml of the subject fluid.

* * * * *